US012778403B2

(12) United States Patent
Ding et al.

(10) Patent No.: US 12,778,403 B2
(45) Date of Patent: Nov. 3, 2026

(54) ENDOSCOPE CLEANING DEVICE

(71) Applicant: Covidien LP, Mansfield, MA (US)

(72) Inventors: Weijiang Ding, Shanghai (CN); Syed Sarfraz Ahamed, Shanghai (CN); Kai Huang, Shanghai (CN)

(73) Assignee: Covidien LP, Mansfield, MA (US)

( * ) Notice: Subject to any disclaimer, the term of this patent is extended or adjusted under 35 U.S.C. 154(b) by 624 days.

(21) Appl. No.: 18/020,666

(22) PCT Filed: Aug. 14, 2020

(86) PCT No.: PCT/CN2020/109139
§ 371 (c)(1),
(2) Date: Feb. 10, 2023

(87) PCT Pub. No.: WO2022/032631
PCT Pub. Date: Feb. 17, 2022

(65) Prior Publication Data

US 2023/0263382 A1 Aug. 24, 2023

(51) Int. Cl.
*A61B 1/12* (2006.01)
*A61B 1/00* (2006.01)
*A61B 17/34* (2006.01)

(52) U.S. Cl.
CPC .......... *A61B 1/126* (2013.01); *A61B 1/00135* (2013.01); *A61B 2017/3419* (2013.01); *A61B 17/3423* (2013.01)

(58) Field of Classification Search
CPC ......... A61B 1/126; A61B 1/127; A61B 1/015; A61B 1/00154; A61B 1/00135; A61B 1/00094; A61B 2090/701; A61B 17/34; A61B 17/3423; A61B 2017/3419; A61B 2017/3437; A61B 2017/00566
See application file for complete search history.

(56) References Cited

U.S. PATENT DOCUMENTS 4,254,762 A * 3/1981 Yoon .................. A61B 17/3496 600/164
4,624,243 A * 11/1986 Lowery .............. A61B 1/00165 600/114
5,354,302 A * 10/1994 Ko ...................... A61B 1/00087 604/161
5,392,766 A 2/1995 Masterson
(Continued)

FOREIGN PATENT DOCUMENTS

CN 203234719 U 10/2013
CN 105491935 A 4/2016
CN 105534471 A 5/2016

OTHER PUBLICATIONS

International Search Report and Written Opinion dated May 12, 2021, issued in corresponding international application No. PCT/CN2020/109139, 11 pages.

*Primary Examiner* — Ryan N Henderson
(74) *Attorney, Agent, or Firm* — Dymera IP, LLC

(57) ABSTRACT

A cleaning device (100) enables cleaning of a lens (18) of an endoscope (10) during a surgical procedure to maintain a clear image without having to remove the endoscope (10) from the patient's body. The cleaning device (100) includes a suction ring (500) that selectively encloses the lens (18) of the endoscope (10) and retains the cleaning fluid during cleaning of the lens (18).

20 Claims, 13 Drawing Sheets

(56) References Cited

U.S. PATENT DOCUMENTS

| | | | | | |
|---|---|---|---|---|---|
| 5,406,940 | A * | 4/1995 | Melzer | A61B 17/3496 | 600/106 |
| 5,467,762 | A * | 11/1995 | Sauer | A61B 17/34 | 604/164.08 |
| 5,578,053 | A * | 11/1996 | Yoon | A61B 10/0233 | 606/165 |
| 5,645,556 | A * | 7/1997 | Yoon | A61B 17/3417 | 604/164.09 |
| 5,665,072 | A * | 9/1997 | Yoon | A61B 17/3496 | 604/164.12 |
| 5,779,680 | A * | 7/1998 | Yoon | A61B 17/3417 | 604/164.12 |
| 8,550,988 | B2 | 10/2013 | Pribanic | | |
| 8,915,842 | B2 * | 12/2014 | Weisenburgh, II | A61B 1/3132 | 600/156 |
| 9,039,604 | B2 * | 5/2015 | Yoshida | A61B 17/3474 | 604/266 |
| 9,078,694 | B2 * | 7/2015 | Hartoumbekis | A61B 1/126 | |
| 9,345,386 | B1 | 5/2016 | Cheng | | |
| 11,051,851 | B2 * | 7/2021 | Einarsson | A61B 1/00096 | |
| 11,412,921 | B2 * | 8/2022 | Holsten | A61L 2/16 | |
| 11,583,176 | B2 * | 2/2023 | Aluru | A61B 17/34 | |
| 11,751,759 | B2 * | 9/2023 | Burt | A61B 17/34 | 600/117 |
| 11,805,968 | B2 * | 11/2023 | Aluru | A61B 17/3417 | |
| 12,150,619 | B2 * | 11/2024 | Holsten | A61L 2/16 | |
| 12,150,625 | B2 * | 11/2024 | Aluru | A61B 1/126 | |
| 2003/0130565 | A1 * | 7/2003 | Muller | A61B 1/00135 | 600/156 |
| 2006/0293559 | A1 | 12/2006 | Grice, III | | |
| 2007/0282253 | A1 * | 12/2007 | Sasaki | A61B 1/313 | 604/93.01 |
| 2008/0045859 | A1 * | 2/2008 | Fritsch | A61B 18/148 | 600/567 |
| 2008/0081948 | A1 * | 4/2008 | Weisenburgh | A61B 1/126 | 600/157 |
| 2008/0255424 | A1 * | 10/2008 | Durgin | A61B 10/0283 | 600/156 |
| 2009/0234193 | A1 * | 9/2009 | Weisenburgh, II | A61B 1/00068 | 600/157 |
| 2009/0299137 | A1 * | 12/2009 | Gal | A61B 1/128 | 600/116 |
| 2010/0010310 | A1 * | 1/2010 | Weisenburgh, II | A61B 1/3132 | 600/156 |
| 2012/0101337 | A1 * | 4/2012 | Clark | A61B 1/00091 | 600/157 |
| 2013/0041230 | A1 * | 2/2013 | Hartoumbekis | A61B 17/3421 | 600/205 |
| 2013/0053643 | A1 * | 2/2013 | Yoshida | A61B 1/126 | 600/114 |
| 2013/0150670 | A1 * | 6/2013 | O'Prey | A61B 1/122 | 600/127 |
| 2013/0150674 | A1 * | 6/2013 | Haig | A61B 1/00135 | 600/155 |
| 2014/0261545 | A1 | 9/2014 | Jenkins | | |
| 2015/0190041 | A1 * | 7/2015 | Suehara | A61B 1/127 | 600/109 |
| 2018/0014908 | A1 * | 1/2018 | Katz | A61B 1/00135 | |
| 2018/0344427 | A1 * | 12/2018 | Rosenbaum | A61B 90/70 | |
| 2019/0125176 | A1 * | 5/2019 | Burt | G02B 23/2476 | |
| 2019/0133676 | A1 * | 5/2019 | Hsu | A61B 18/1485 | |
| 2020/0100811 | A1 * | 4/2020 | Holsten | A61B 1/126 | |
| 2020/0163541 | A1 * | 5/2020 | Holsten | A61L 2/16 | |
| 2020/0214549 | A1 * | 7/2020 | Hurst | A61B 17/3421 | |
| 2021/0127963 | A1 * | 5/2021 | Aluru | A61B 17/3421 | |
| 2021/0127964 | A1 * | 5/2021 | Aluru | A61B 17/34 | |
| 2021/0219832 | A1 * | 7/2021 | Retailleau | A61B 1/05 | |
| 2021/0236749 | A1 * | 8/2021 | Kokhanenko | A61B 17/3462 | |
| 2021/0322684 | A1 * | 10/2021 | Fischer | A61M 13/003 | |
| 2022/0079625 | A1 * | 3/2022 | Einarsson | A61B 90/361 | |
| 2022/0175237 | A1 * | 6/2022 | De Abreu | A61B 1/00135 | |
| 2022/0192480 | A1 * | 6/2022 | Burt | A61B 1/00006 | |
| 2022/0386859 | A1 * | 12/2022 | Holsten | A61B 90/70 | |
| 2023/0165452 | A1 * | 6/2023 | Ding | A61B 1/00135 | 600/114 |
| 2023/0414085 | A1 * | 12/2023 | Aluru | A61B 17/3417 | |
| 2024/0293018 | A1 * | 9/2024 | Aluru | A61L 2/16 | |

* cited by examiner

ENDOSCOPE CLEANING DEVICE

TECHNICAL FIELD

The disclosure relates to a minimally invasive viewing instrument and, more particularly, to an endoscope cleaning device for removing debris from a lens of the endoscope and a method of use thereof.

BACKGROUND

Minimally invasive surgery eliminates the need to make a large incision in a patient, thereby reducing discomfort, recovery time, and many of the deleterious side effects associated with traditional open surgery. Minimally invasive viewing instruments such as, e.g., laparoscopes and endoscopes, provide viewing of internal tissues and/or organs during the minimally invasive surgery.

Laparoscopic surgery involves the placement of a laparoscope in a small incision in the abdominal wall of a patient, to view the surgical site. Endoscopic surgery involves the placement of an endoscope in a naturally occurring orifice, e.g., mouth, nose, anus, urethra, or vagina, to view the surgical site. Other minimally invasive surgical procedures include video assisted thoracic surgery and cardiovascular surgery conducted through small incisions between the ribs. These procedures also utilize scopes to view the surgical site.

A typical minimally invasive viewing instrument, e.g., a laparoscope or an endoscope, includes a housing, an elongated lens shaft extending from one end of the housing, and a lens that is provided in a distal end of the elongated lens shaft. A camera viewfinder extends from the other end of the housing. A camera is connected to the housing and transmits images sighted through the lens to an external monitor on which the images are displayed. During a surgical procedure, the distal end portion of the elongated lens shaft is extended into the patient, while the proximal end portion of the elongated lens shaft, the housing and the camera viewfinder remain outside the patient. In this manner, the laparoscope/endoscope is positioned and adjusted to view particular anatomical structures in the surgical field on the monitor.

During insertion of an endoscope or a laparoscope into the body and during the surgical procedure, debris, e.g., organic matter and/or moisture, may be deposited on the lens of the scope. The buildup of debris and condensation on the lens impairs visualization of the surgical site, and often necessitates cleaning of the lens.

SUMMARY

The disclosure describes a cleaning device of use with an endoscope that demonstrates a practical approach to meeting the performance requirements and overcoming usability challenges associated with cleaning a lens of an endoscope during a surgical procedure.

In accordance with this disclosure, a cleaning device for use with an endoscope includes a housing detachably securing the endoscope thereto, an elongate shaft extending distally from the housing, an inner tube disposed within a lumen of the elongate shaft, and a suction ring coupled to a distal end portion of the elongate shaft. The housing includes an inlet port, an outlet port, and a slider slidably received in the housing. The lumen of the elongate shaft is in communication with the housing. The elongate shaft is coupled to the slider for concomitant axial displacement therewith. The endoscope is received in the inner tube. The slider is transitionable between a first position, in which, the slider closes the inlet and outlet ports and a lens of the endoscope is distal of the suction ring, and a second position, in which, the slider is in communication with the inlet port to provide a cleaning fluid to the lens of the endoscope enclosed by the suction ring.

In an aspect, the elongate shaft may define first and second grooves that define inlet and outlet channels with the inner tube.

In another aspect, the inner tube may include holes in a distal portion of the inner tube such that the cleaning fluid flowing distally through the inlet channel enters the inner tube and flows across the lens of the endoscope.

In yet another aspect, the cleaning fluid flowing across the lens of the endoscope may be retained in the suction ring prior to flowing towards the outlet port of the housing.

In still yet another aspect, the outlet port of the housing may be coupled to a vacuum source such that the suction ring retains the cleaning fluid when the slider is in the second position.

In an aspect, the inlet and outlet channels may be in communication with the respective inlet and outlet ports of the housing when the slider is in the second position.

In another aspect, the slider may define first and second fluid passages in communication with the inlet and outlet channels, respectively.

In yet another aspect, the first and second fluid passages may be in registration with the inlet and outlet ports of the housing when the slider is in the second position.

In still yet another aspect, the inlet and outlet ports of the housing may be coupled to a cleaning fluid supply and a vacuum source, respectively.

In an aspect, the inner tube may extend into the suction ring.

In another aspect, the suction ring may include a weakened portion configured to close an opening defined by the suction ring.

In yet another aspect, the slider may be biased towards the first position.

In accordance with another aspect of the disclosure, a method of cleaning an endoscope includes placing an endoscope in a cleaning device such that a lens of the endoscope is disposed distal of a suction ring mounted on a distal end portion of an elongate shaft of the cleaning device; securing the endoscope to a housing of the cleaning device to inhibit relative movement between the housing and the endoscope; transitioning a slider disposed in the housing from a first position, in which, the slider closes inlet and outlet ports of the housing, to a second position, in which, the slider is in fluid communication with the inlet and outlet ports and the elongate shaft is advanced to enclose the lens of the endoscope by the suction ring; supplying a cleaning fluid to the lens of the endoscope to remove debris from the lens while retaining the cleaning fluid within the suction ring; and removing the cleaning fluid from the suction ring through the outlet port.

In an aspect, retaining the cleaning fluid within the suction ring may include connecting the outlet port of the housing to a vacuum source.

In another aspect, transitioning the slider may include pulling a trigger disposed on the housing that includes a pusher rotatably coupled to the trigger such that pulling of the trigger rotates the pusher to cause axial displacement of the slider.

In yet another aspect, supplying the cleaning fluid may include connecting the inlet port to a cleaning fluid supply.

In still yet another aspect, supplying the cleaning fluid may include closing an opening of the suction ring by a vacuum source to retain the cleaning fluid within the suction ring.

In accordance with another aspect of the disclosure, a method of cleaning an endoscope including placing a portion of an endoscope in a cleaning device such that a lens of the endoscope is disposed distal of a suction ring mounted on a distal end portion of the cleaning device; axially displacing an elongate shaft of the cleaning device to place the lens of the endoscope within the suction ring; applying suction to the suction ring to close an opening defined by the suction ring to form a fluid tight seal; applying a cleaning fluid to the lens of the endoscope to remove debris from the lens while retaining the cleaning fluid within the suction ring; and removing the cleaning fluid from the suction ring through an outlet port of a housing of the cleaning device.

In an aspect, axially displacing the elongate shaft may include axially displacing a slider disposed within the housing of the cleaning device such that the slider is in fluid communication with an inlet port and the outlet port of the housing.

In another aspect, the method may further include supplying the cleaning fluid to the inlet port of the housing and applying suction to the outlet port of the housing.

BRIEF DESCRIPTION OF DRAWINGS

The above and other aspects and features of this disclosure will become more apparent in view of the following detailed description when taken in conjunction with the accompanying drawings wherein like reference numerals identify similar or identical elements.

DETAILED DESCRIPTION

Figures 1, 1A:
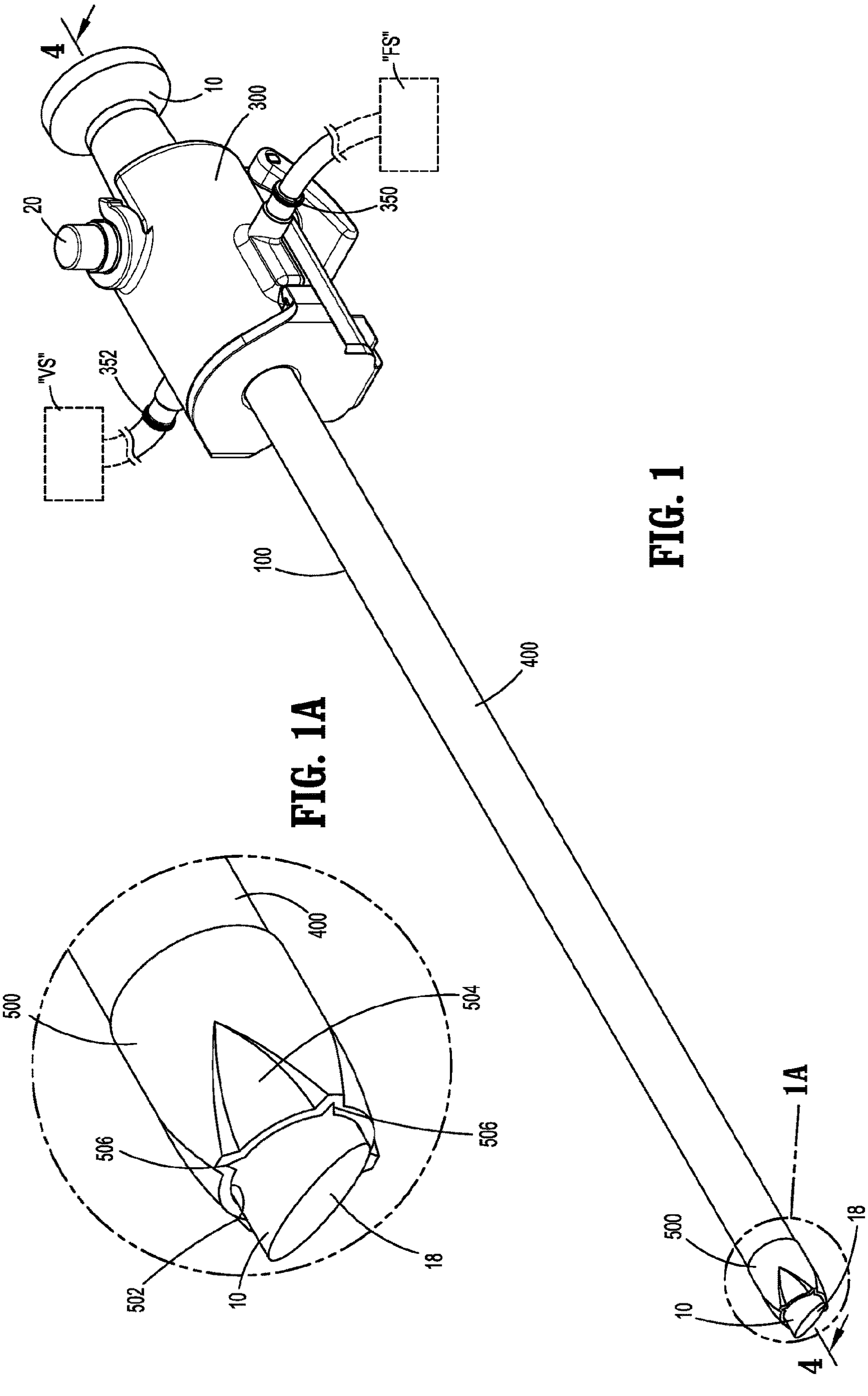
FIG. 1 is a perspective view of a cleaning device in accordance with the disclosure, illustrating use with an endoscope.
FIG. 1A is an enlarged view of the indicated area of detail of FIG. 1.

The endoscope cleaning device disclosed herein is described in detail with reference to the drawings, in which like reference numerals designate identical or corresponding elements in each of the several views.

As used herein, the term "distal" refers to the portion that is being described which is farther from a user, while the term "proximal" refers to the portion that is being described which is closer to a user. In addition, the terms parallel and perpendicular are understood to include relative configurations that are substantially parallel and substantially perpendicular up to about + or −10 degrees from true parallel and true perpendicular. Further, to the extent consistent, any or all of the aspects detailed herein may be used in conjunction with any or all of the other aspects detailed herein.

In FIGS. 1 and 1A, an exemplary in situ lens cleaning device in accordance with the disclosure is shown generally as a cleaning device 100. The cleaning device 100 enables cleaning of a lens 18 of an endoscope 10 during a surgical procedure to maintain a clear image without having to remove the endoscope 10 from the patient's body. Further the cleaning device 100 enables use of cleaning fluids without increased risk of, e.g., tumor spread and air/gas embolism, by retaining the used cleaning fluids within the cleaning device 100, as will be discussed below. The cleaning device 100 includes a housing 300, an elongate shaft 400 extending distally from the housing 300, and a suction ring 500 mounted on a distal end portion of the elongate shaft 400. The suction ring 500 is adjustable to enable passage of the endoscope 10 therethrough and to retain cleaning fluids used to clean the lens 18 of the endoscope 10 therein, as will be discussed hereinbelow.

Figure 2:
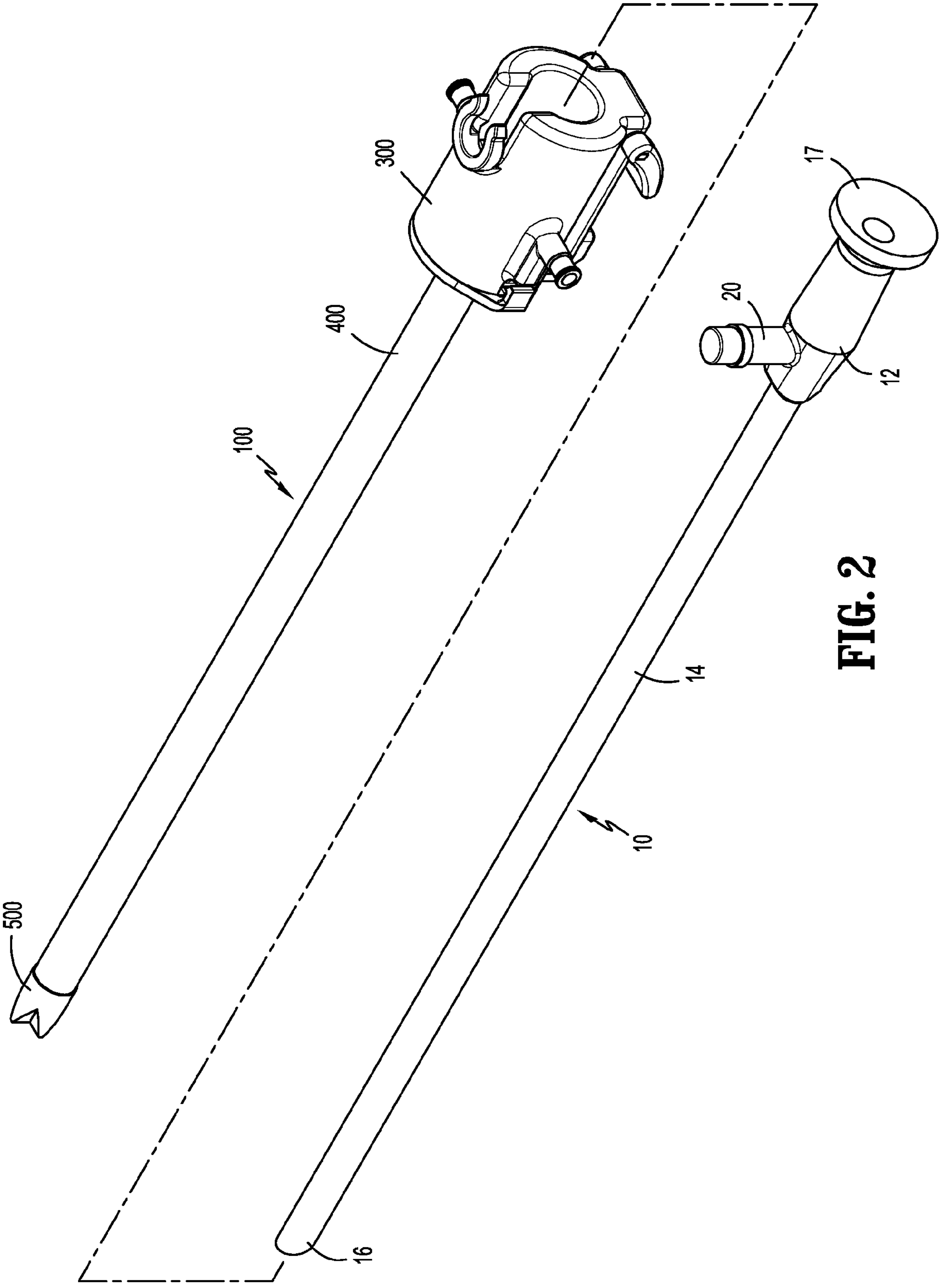
FIG. 2 is a perspective assembly view of the cleaning device and the endoscope of FIG. 1.

FIG. 2 illustrates the endoscope 10 and the cleaning device 100 separated prior to use. In particular, the endoscope 10 includes a housing 12 and an elongated tubular shaft 14 extending distally from the housing 12 and terminating in the lens 18 (FIG. 1A). A distal tip portion 16 of the endoscope 10 includes a number of optical components that produce images of the patient's tissues as known by one skilled in the art. The optical components generally include a window or front element of a lens assembly that is positioned in front of an image sensor (not shown) or in front of a fiber optic imaging guide that transfers an image to the proximal end of the endoscope 10. Illumination sources such as, e.g., light-emitting diodes, fiber optic or illumination guides, may also be provided. The elongate tubular shaft 14 may be rigid, semi-rigid, or flexible. The housing 12 includes a connector 20 configured to receive, e.g., a cable, therethrough, and a viewfinder 17 adapted to sight images of a surgical field in the patient, e.g. an abdominal cavity, thoracic cavity, etc., as the position of the endoscope 10 is adjusted to view a particular anatomical structure in the surgical field. A camera is adapted to receive images of the surgical field sighted through the lens 18 and transmit the images to, e.g., an external monitor, on which the images of the surgical field are displayed. That is, a visual display device converts the optical signal into a video signal to produce a video image on the monitor (or for storage on select media). Accordingly, the monitor enables a clinician to view the anatomical structure in the surgical field inside the patient as the surgical procedure is carried out using minimally invasive or endoscopic surgical instruments. Throughout the surgical procedure, condensation, smoke particles, and biological tissue or matter have a tendency to contact and build up on the lens 18 of the endoscope 10. This tends to obscure the images of the surgical field as they are displayed on the monitor. To this end, the cleaning device 100 that enables cleaning of the lens 18 during the surgical procedure to maintain a clear image without having to remove the endoscope 10 from the patient's body may be utilized with the endoscope 10, as will be discussed hereinbelow.

Figure 3:
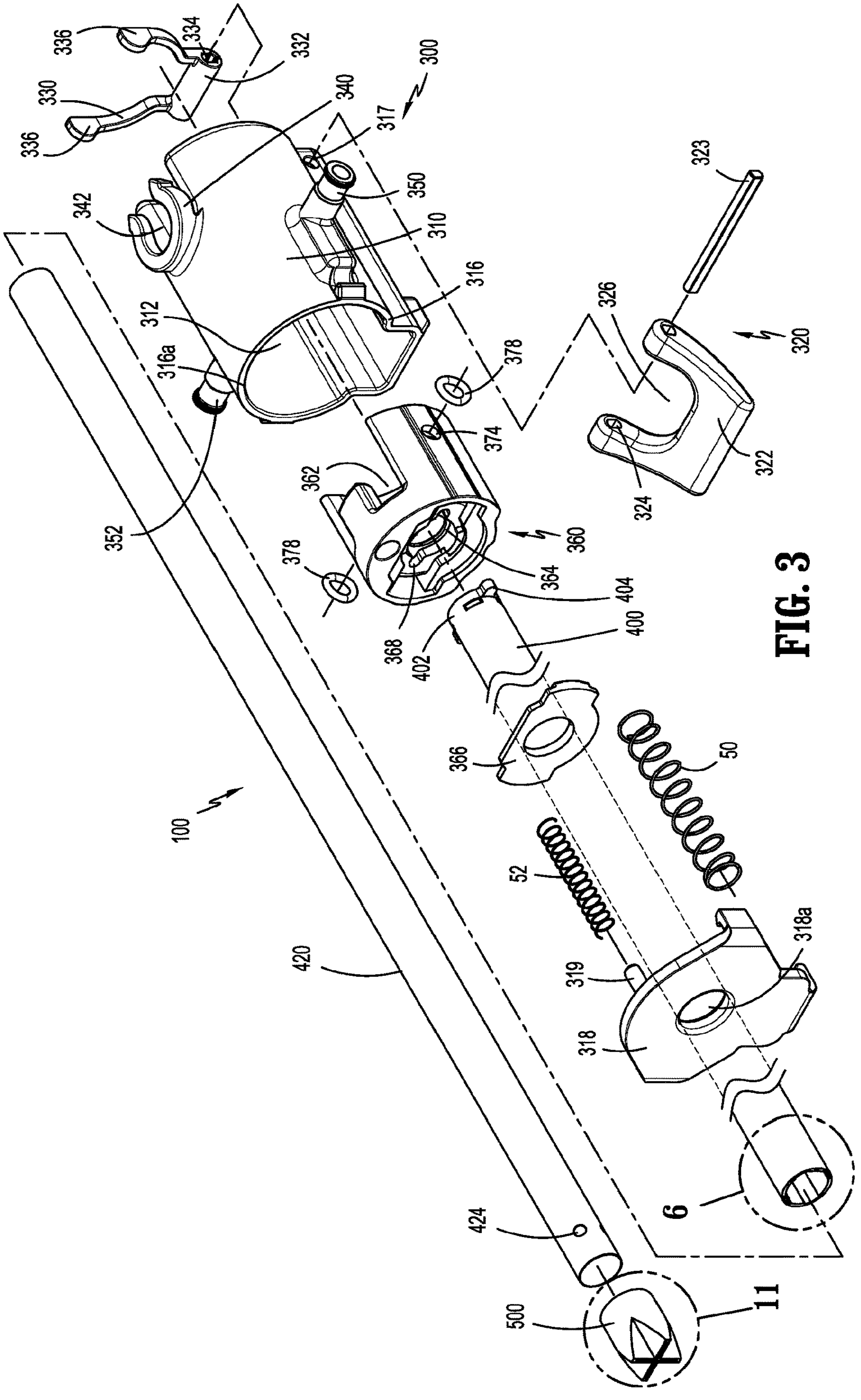
FIG. 3 is an exploded perspective view of the cleaning device of FIG. 1 with parts separated.
Figure 14:
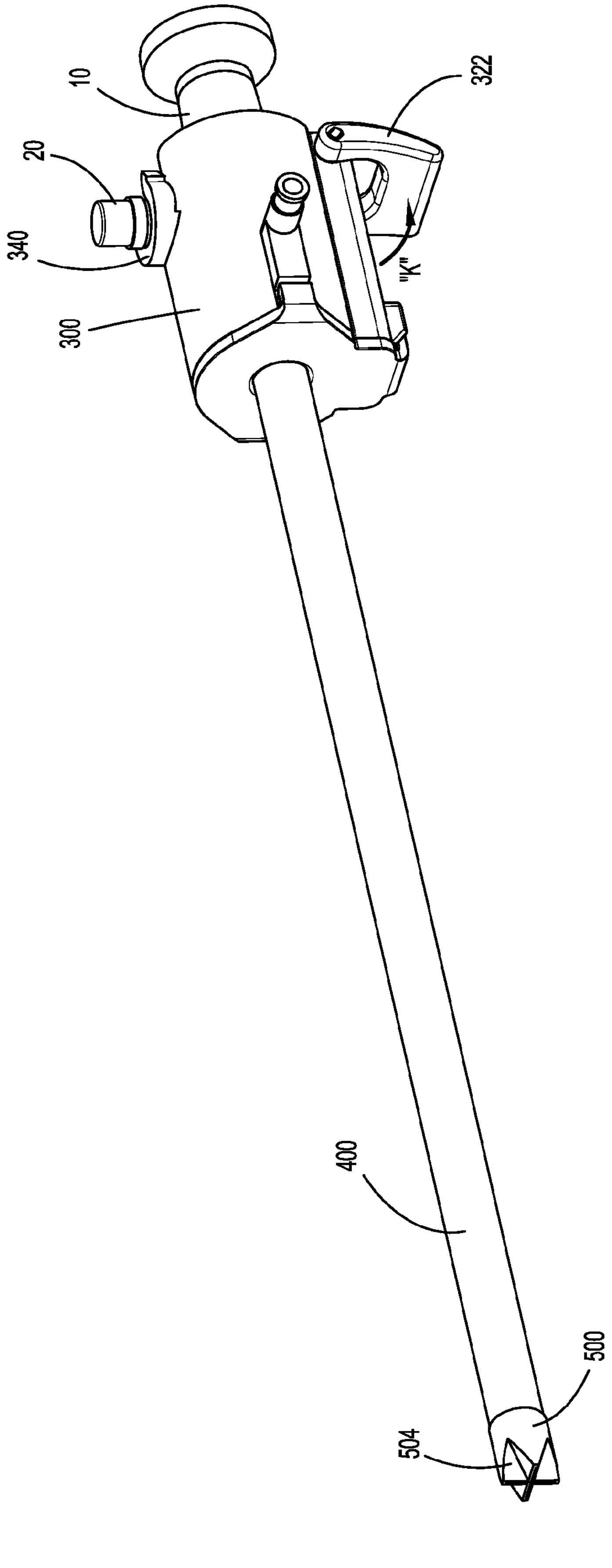
FIG. 14 is a perspective view of the cleaning device and the endoscope of FIG. 1 in the closed configuration.

FIG. 3 illustrates the cleaning device 100 including the suction ring 500 that adjustably receives the endoscope 10 therethrough (FIG. 1) and retains the cleaning fluids therein (FIG. 14). The cleaning device 100 includes the housing 300, the elongate shaft 400 extending distally from the housing 300, and the suction ring 500 mounted on a distal portion of the elongate shaft 400. The housing 300 includes a body 310 having inlet and outlet ports 350, 352 connected to a fluid supply "FS" (FIG. 1) and a vacuum source "VS" (FIG. 1), respectively. The body 310 includes a retaining portion 340 defining a slot 342. The slot 342 is configured to receive the connector 20 (FIG. 1) of the endoscope 10 therein to inhibit relative rotational motion therebetween. The retaining portion 340 may be formed of a flexible or resilient material such as, e.g., an elastomer or a polymer, to detachably secure the connector 20 to the retaining portion 340 by, e.g., snap fit or friction fit, configuration. The body 310 defines a lumen 312 configured to receive a slider 360 slidably disposed therein. The body 310 further includes a trigger assembly 320 including a trigger 322 pivotably coupled to a pusher 330 by a pivot pin 323 having a non-circular cross-section such that rotation of the trigger 322 in a first direction rotates the pusher 330 in a second direction opposite of the first direction. In particular, the trigger 322 defines a cutout 326 configured receive a portion of the body 310 in the cutout 326, and bores 324 receiving the pivot pin 323. The pusher 330 includes a base 332 that is received in the body 310. The base 332 defines a bore 334 aligned with a bore 316 defined in the body 310 to receive the pivot pin 323 therethrough. The pusher 330 further includes fingers 336 that rotate with the base 332 to engage the slider 360 to cause axial displacement of the slider 360, as will be discussed hereinbelow.

FIG. 3 further illustrates the slider 360 slidably disposed within the body 310. The slider 360 includes a channel 362 to receive at least a portion of the endoscope 10 (FIG. 2) therein. The slider 360 further includes an engaging portion 364 configured to engage a proximal end portion 402 of the elongate shaft 400. For example, the engaging portion 364 and the distal end portion 402 of the elongate shaft 400 may have complementary cross-sections to enhance securement therebetween and to inhibit relative movement such as, e.g., rotation, therebetween. For example, the distal end portion 402 may include protuberances 404 that extend radially outwards. The protuberances 404 engage the engaging portion 364 of the slider 360. For example, the engaging portion 364 may define recesses 368 configured to receive the protuberances 404. The protuberances 404 may diametrically oppose each other to enhance securement with the engaging portion 364 of the slider 360. The body 310 further includes a slider cap 366 that encloses the protuberances 404 in the engaging portion 364 of the slider 360. In this manner, the elongate shaft 400 is coupled to the slider 360 as a single construct such that axial displacement of the slider 360 imparts concomitant axial displacement to the elongate shaft 400.

Figure 4:
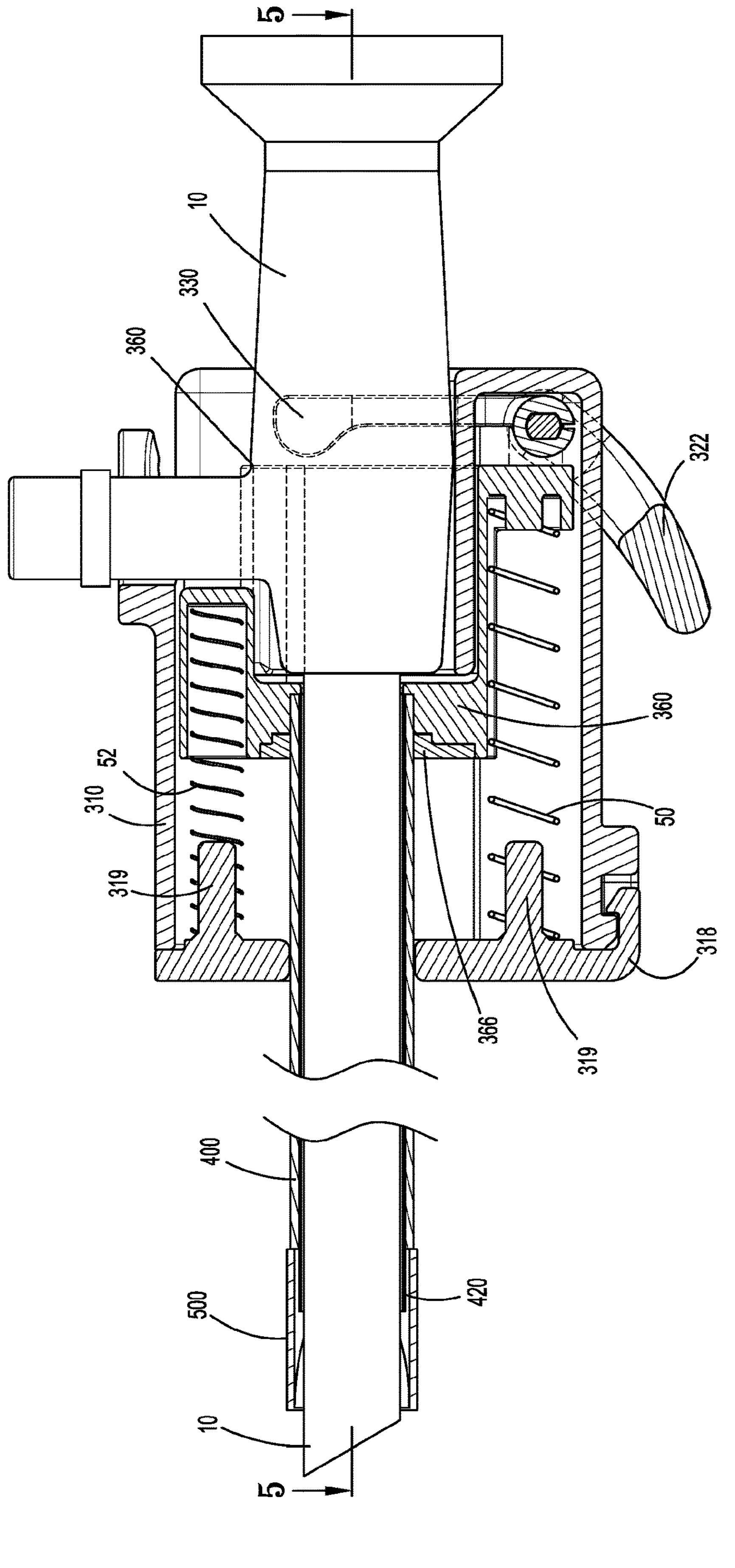
FIG. 4 is a partial cross-sectional view of the cleaning device and the endoscope of FIG. 1 taken along section line 4-4 of FIG. 1.
Figure 5:
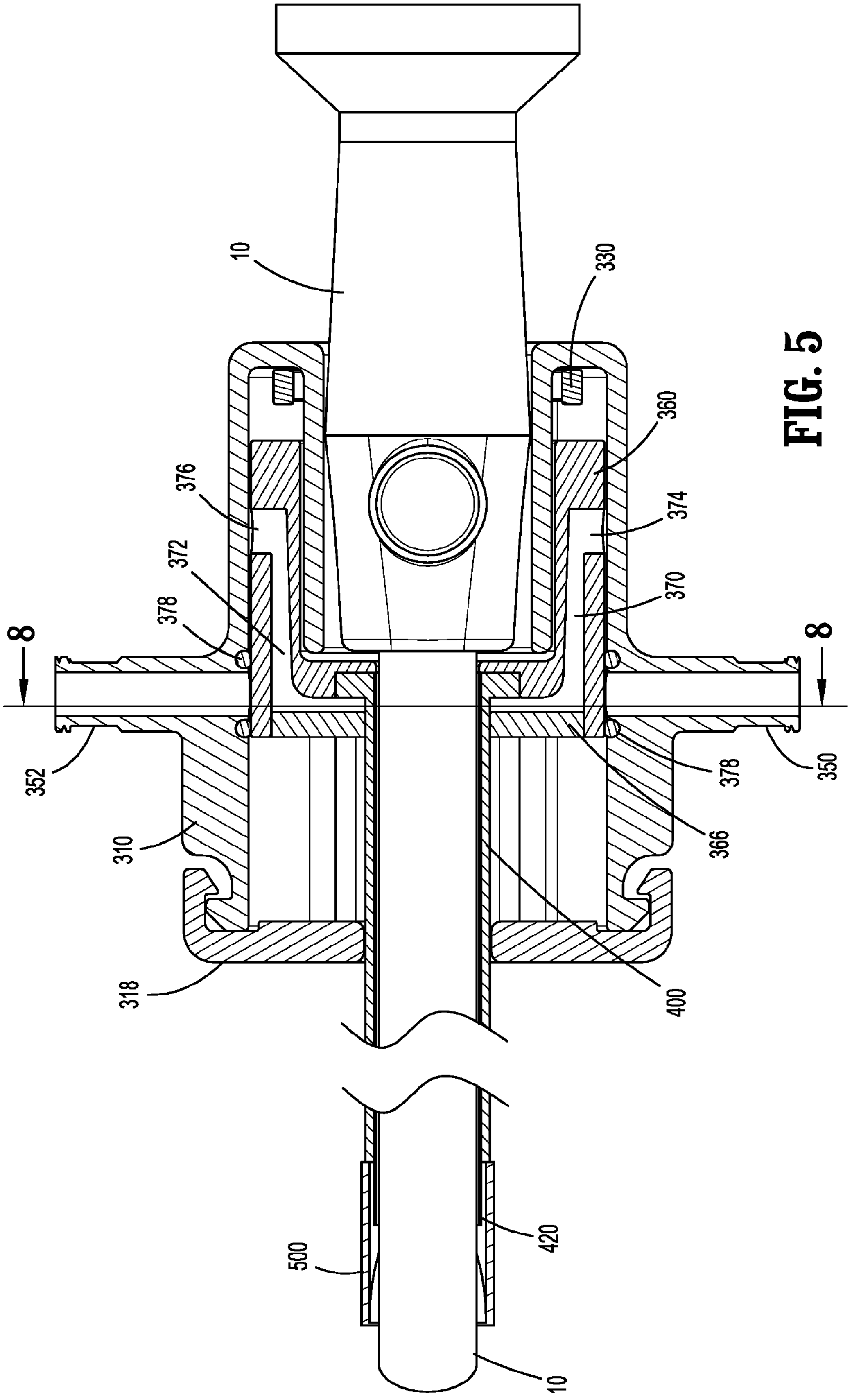
FIG. 5 is a partial cross-sectional view of the cleaning device and the endoscope of FIG. 4 taken along section line 5-5 of FIG. 4.

FIGS. 4 and 5 illustrate the slider 360 slidably disposed within the body 310. The slider 360 includes first and second fluid passages 370, 372 in communication with first and second openings 374, 376, respectively. The first and second openings 374, 376 may be selectively aligned with the inlet and outlet ports 350, 352 of the body 310 (FIG. 13), respectively, as will be discussed hereinbelow. The body 310 further includes seals 378 such as, e.g., O-rings, that are positioned about the respective first and second openings 374, 376 to form a seal against the slider 360. The mouth 316 (FIG. 3) of the body 310 defines an opening **316*a*. The body 310 includes a cover 318 defining a bore 318*a* (FIG. 3) receiving the elongate shaft 400 therethrough. The cover 318 includes bosses 319 that secure springs 50, 52 thereto (FIG. 4). In particular, the springs 50, 52 are secured to the respective bosses 319 of the cover 318 and the slider 360 such that the slider 360** is biased towards a proximal-most position.

Figure 6:
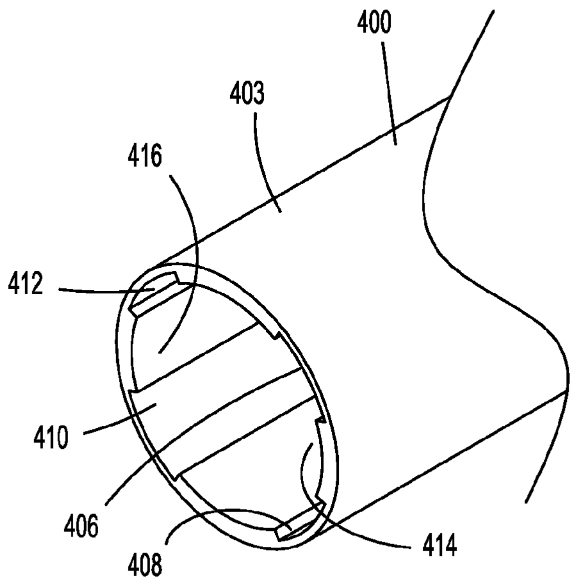
FIG. 6 is an enlarged view of the indicated area of detail of FIG. 3.
Figure 7:
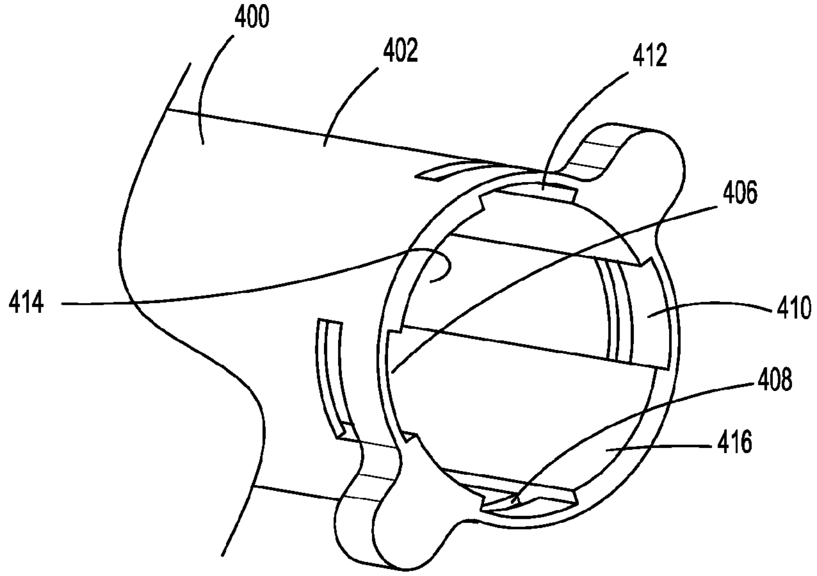
FIG. 7 is a partial perspective view of an elongate shaft of the cleaning device of FIG. 1, illustrating a proximal end portion of the elongate shaft.
Figure 8:
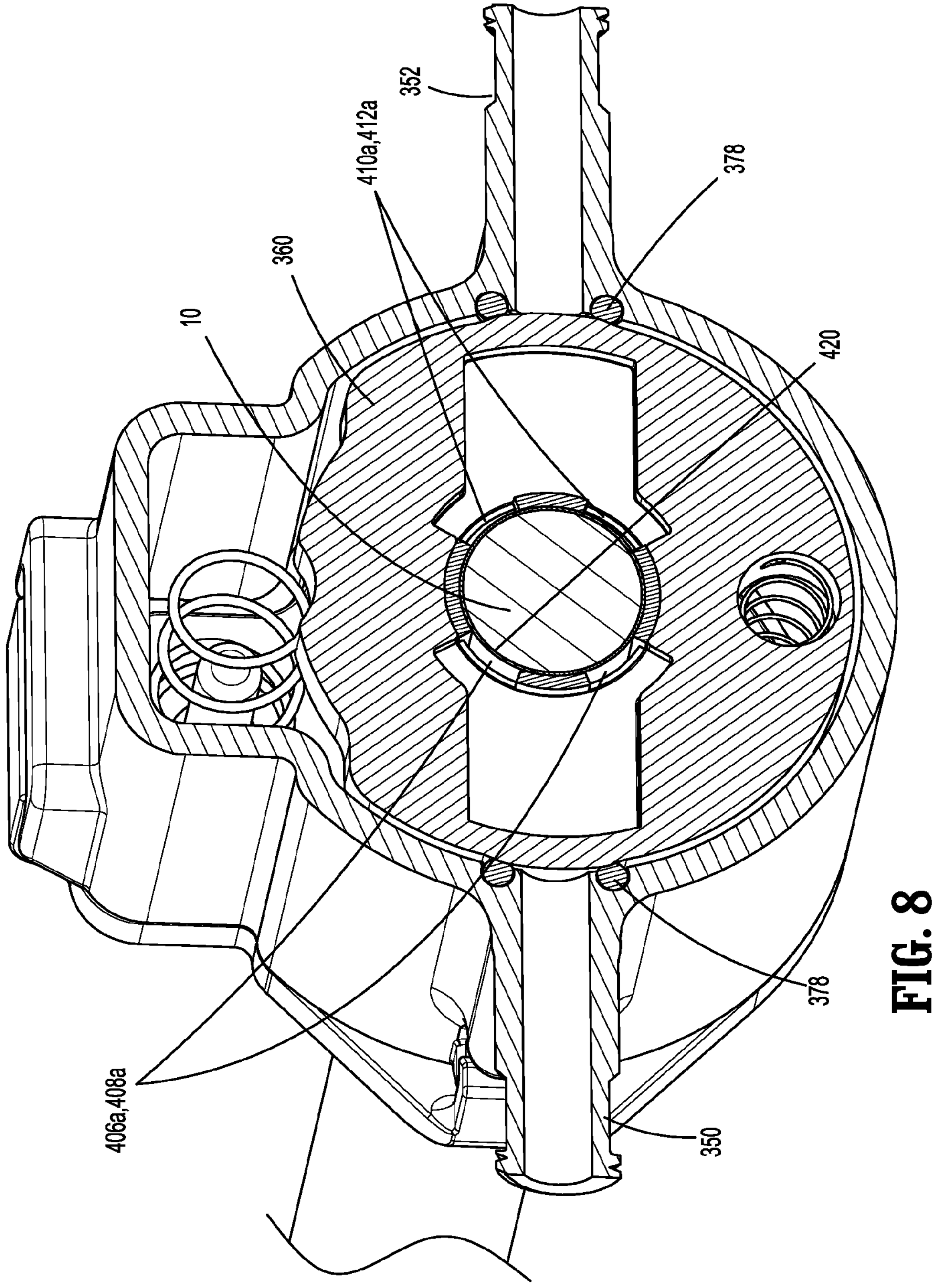
FIG. 8 is a perspective view of a housing of the cleaning device taken along section line 8-8 of FIG. 5.
Figure 9:
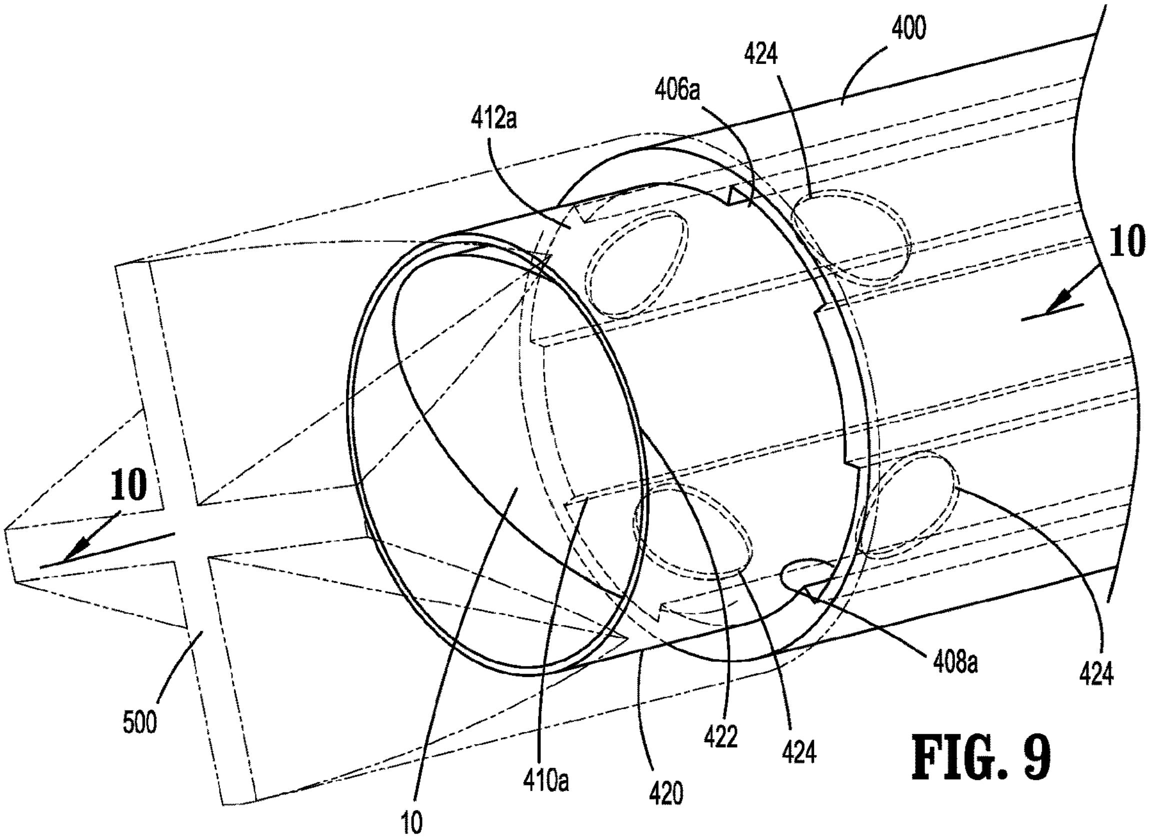
FIG. 9 is a partial perspective view of the cleaning device and the endoscope of FIG. 1, illustrating a suction ring in a closed configuration.

FIGS. 6 and 7 illustrate the elongate shaft 400 defining a lumen 414 therethrough and inner grooves 406, 408, 410, 412 extending along a length of the elongate shaft 400 between the proximal end portion 402 and a distal end portion 403 of the elongate shaft 400. For example, the inner grooves 406, 408, 410, 412 may be circumferentially arranged. FIG. 8 illustrates an inner tube 420 (see also, e.g., FIG. 3) disposed in the lumen 414 (FIG. 7) of the elongate shaft 400. The elongate shaft 400 and the inner tube 420 may be concentrically arranged. In particular, the inner tube 420 is coupled to the slider 360 and extends through the lumen 414 of the elongate shaft 400. The inner tube 420 is further secured with the suction ring 500 (FIG. 5). In particular, at least a portion of the inner tube 420 is received within the suction ring 500 (FIG. 9). The inner tube 420 is dimensioned to engage an inner wall 416 (FIG. 6) of the elongate shaft 400 such that the inner grooves 406, 408, 410, 412 form inlet channels **406*a*, 408*a* and outlet channels 410*a*, 412*a*. The inlet channels 406*a*, 408*a* are in fluid communication with the first fluid passage 370 (FIG. 5) of the slider 360, and the outlet channels 410*a*, 412*a* are in fluid communication with the second fluid passage 372 (FIG. 5) of the slider 360**.

Figure 10:
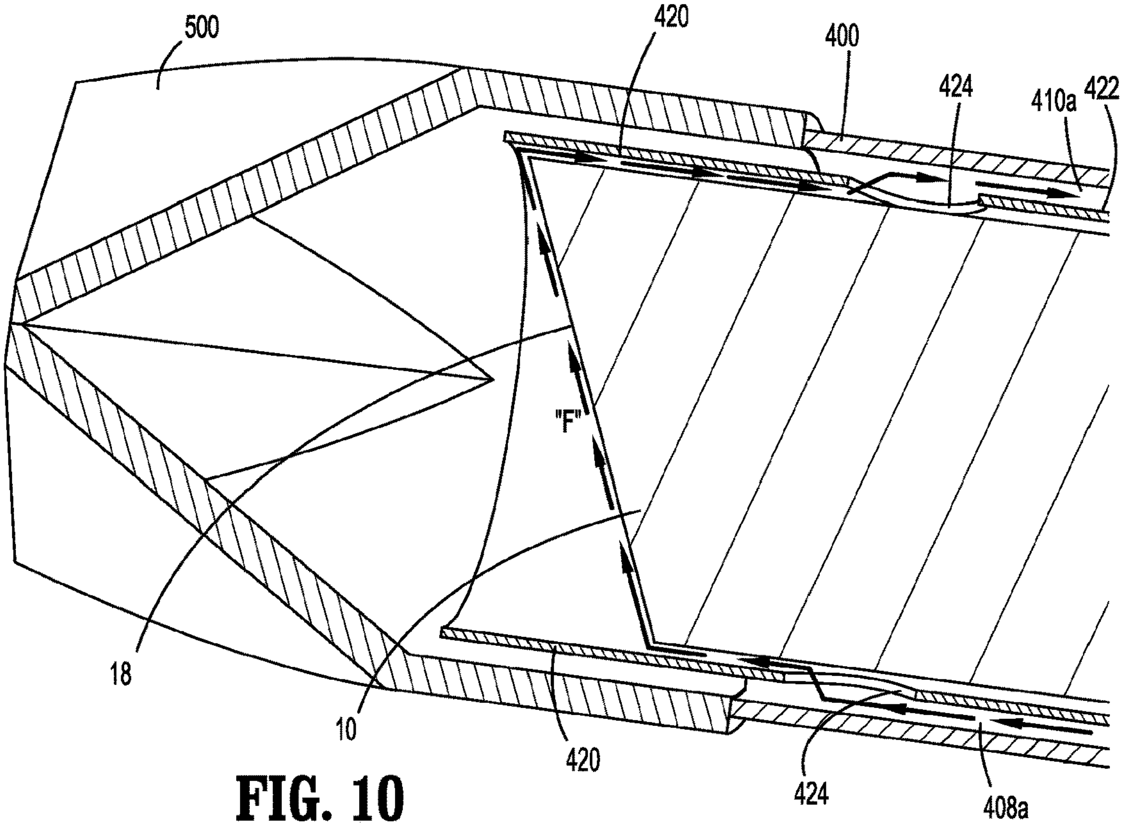
FIG. 10 is a partial perspective view of the cleaning device of FIG. 9 taken along section line 10-10 of FIG. 9.
Figure 13:
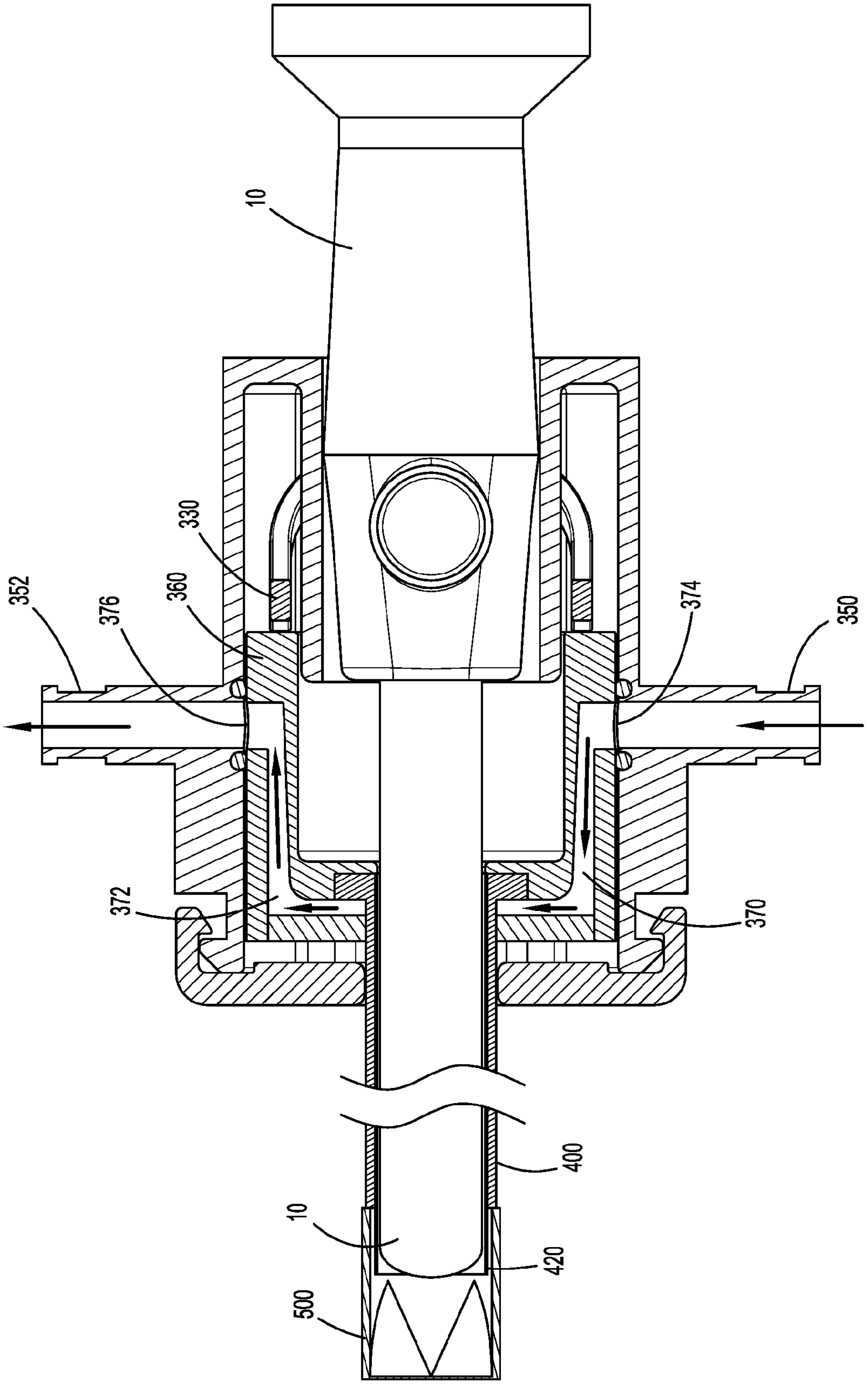
FIG. 13 is a partial cross-sectional view of the cleaning device of FIG. 12 taken along section line 13-13 of FIG. 12.

FIGS. 9 and 10 illustrate a distal end portion 422 of the inner tube 420. The distal end portion 422 defines a plurality of holes 424. Each hole 424 may be in registration with a corresponding inlet or outlet channel **406*a*, 408*a*, 410*a*, 412*a* (shown in phantom) such that two holes 424 are associated with the inlet channels 406*a*, 408*a* and two holes 424 are associated with the outlet channels 410*a*, 412*a*. Under such a configuration, the cleaning fluid may flow distally through the inlet channels 406*a*, 408*a* and enters the inner tube 420 through the holes 424. The cleaning fluid is then directed across the lens 18 of the endoscope 10 in the direction of arrow "F". The cleaning fluid cleans and removes any the debris from the lens 18. The cleaning fluid then flows proximally through a gap defined between the endoscope 10 and the inner tube 420 and exits the inner tube 420 through the corresponding holes 424. The cleaning fluid then flows proximally through the outlet channels 410*a*, 412*a* and the second fluid passage 372 (FIG. 13) of the slider 360 towards the outlet port 352 (FIG. 13**).

FIGS. 9 and 10 also illustrate the inner tube 420 extending distally through the elongate shaft 400. A portion of the inner tube 420 protruding from the elongate shaft 400 supports the suction ring 500 thereon. The suction ring 500 may be, e.g., over-molded, ultrasonically welded, or glued, to the inner tube 420 and/or the elongate shaft 400.

Figure 11:
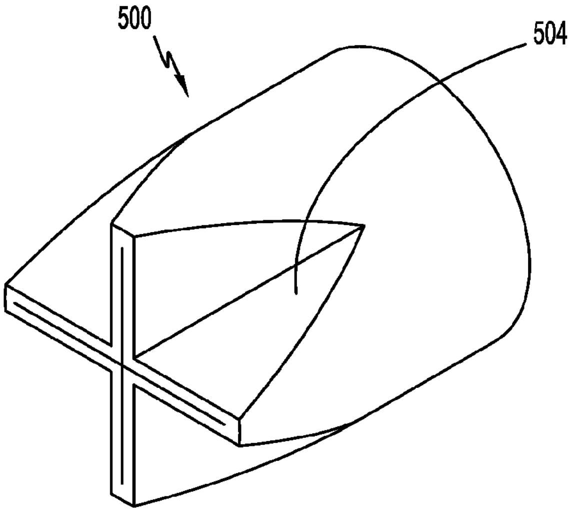
FIG. 11 is a perspective view of a suction ring of the cleaning device of FIG. 1.

FIG. 11 illustrates the suction ring 500. The suction ring 500 may be formed of a flexible or pliable material that may easily transition between an open configuration (FIG. 1A) when the endoscope 10 extends therethrough, and a closed configuration (FIG. 10) when a negative pressure or suction is applied to the suction ring 500 through the outlet port 352 (FIG. 1). The suction ring 500 defines an opening 502 (FIG. 1A) configured to receive the endoscope 10 therethrough. The suction ring 500 includes weakened portions 504 (FIG. 1A) that facilitate transition to the closed configuration. For example, the suction ring 500 may include non-uniform thickness to provide the weakened portions 504. In addition, the suction ring 500 may further define notches 506 (FIG. 1A) circumferentially arranged around the suction ring 500 to close the suction ring 500 in a pre-determined configuration as shown in FIG. 10. The closed configuration of the suction ring 500 provides a fluid tight seal to retain the cleaning fluid and the debris from the lens 18 of the endoscope 10 in the suction ring 500 prior to flowing out through the outlet channel 410*a* (FIG. 8).

Figure 12:
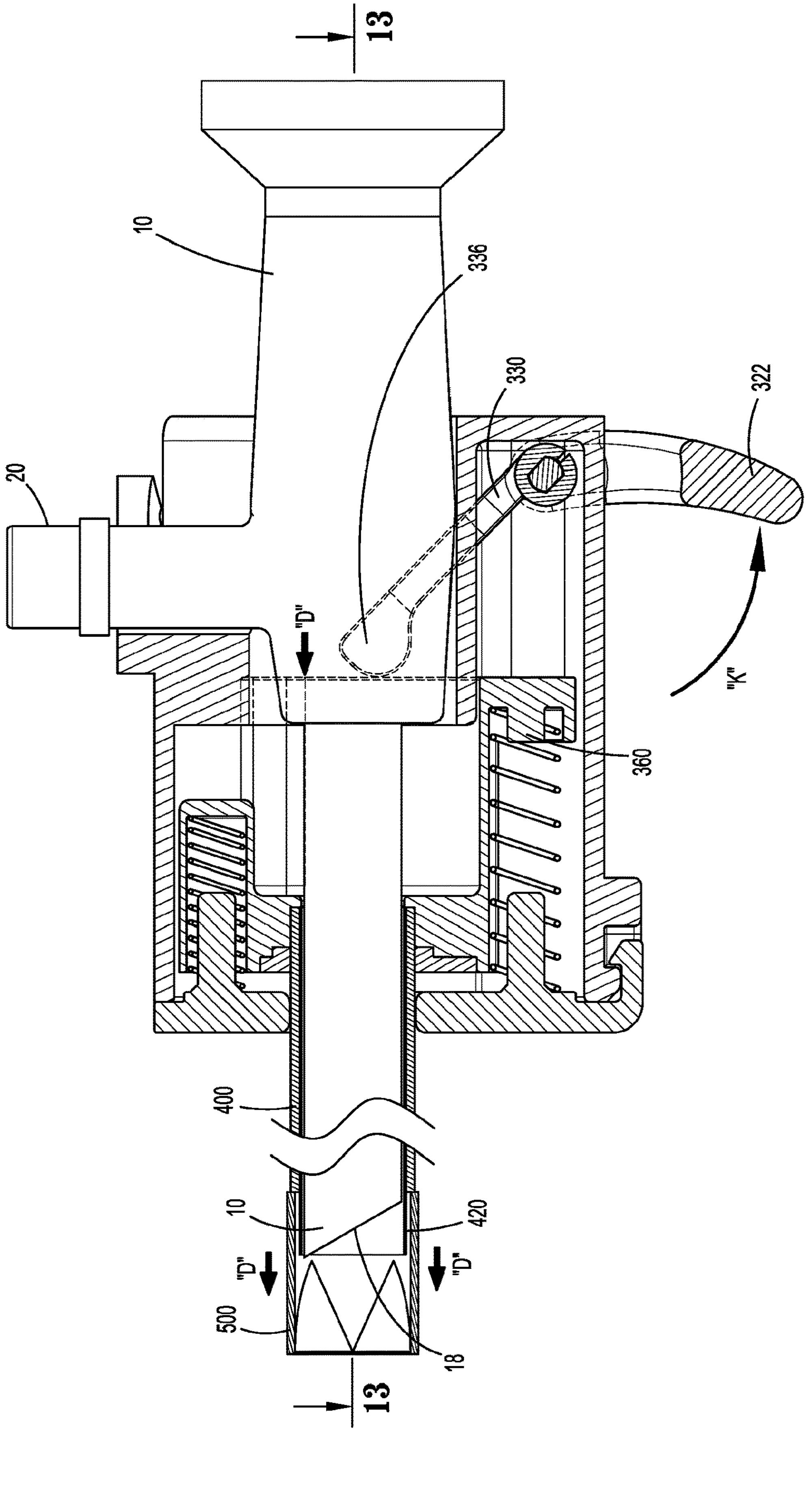
FIG. 12 is a partial cross-sectional view of the cleaning device and the endoscope of FIG. 1 in the closed configuration.
Figure 15:
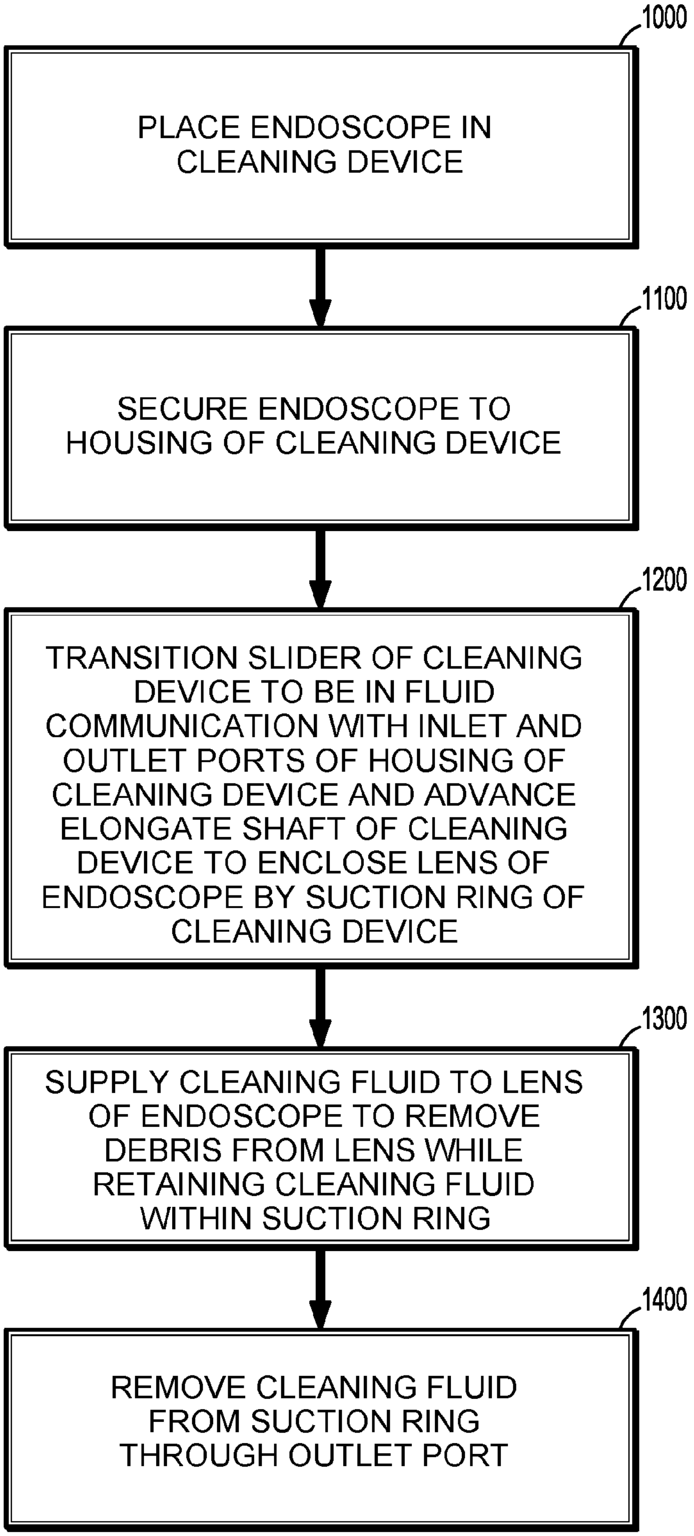
FIG. 15 is a flow chart illustrating a method of using the cleaning device with the endoscope of FIG. 1.

FIG. 15 illustrates a flow chart illustrating a method of cleaning the lens 18 of the endoscope 10 using the cleaning device 100. The connector 20 of the endoscope 10 is placed in the retaining portion 340 of the cleaning device 100 in step 1000. The endoscope 10 is detachably secured with the cleaning device 100 in step 1100. Thereafter, the endoscope 10 and the cleaning device 100 are inserted through an opening in tissue and the lens 18 of the endoscope 10 may be manipulated as needed to be placed adjacent a surgical site. At this time, a desired surgical procedure may be performed utilizing the endoscope 10. When the lens 18 of the endoscope 10 is obscured by debris, e.g., organic matter and/or moisture, the clinician may actuate the cleaning device 100 by pulling the trigger 322 in the direction of an arrow "K" (FIG. 12) in, which, in turn, causes the finger 336 of the pusher 330 to rotate in a direction opposite of the arrow "K". Actuation of the trigger 322 causes axial displacement of the slider 360 in the direction of an arrow "D" relative to the body 310 of the housing 300. At this time, the elongate shaft 400 and the inner tube 420 are displaced axially in the direction of the arrow "D" such that at least a portion of the suction ring 500 is disposed distal of the lens 18 of the endoscope 10. Axial displacement of the slider 360 aligns the first and second openings 374, 376 of the slider 360 with the inlet and outlet ports 350, 352, respectively. In this manner, the inlet portion 350 is in fluid communication with the first fluid passage 370, and the second fluid passage 372 is in fluid communication with the outlet port 352 in step 1200. By connecting the inlet port 350 to a cleaning fluid supply "FS" and the outlet port 352 to a vacuum source "VS," the cleaning fluid may be supplied to the lens 18 of the endoscope through the first fluid passage 370 (FIG. 13) of the slider 360 and the inlet channels 406*a*, 480*a* (FIG. 9) defined by the elongate shaft 400 and the inner tube 420 in step 1300. The cleaning fluid flows across the lens 18 of the endoscope 10 to remove any debris on the lens 18. At this time, the suction ring 500 is in the closed configuration (FIG. 14) through negative pressure or suction provided by the vacuum source "VS" connected to the outlet port 352. Under such a configuration, the cleaning fluid is retained within the suction ring 500. The cleaning fluid cleans the lens 18 and flows towards the outlet port 352 through the outlet channel 410*a*, 412*a* (FIG. 8) defined by the elongate shaft 400 and the inner tube 420 and through the second fluid passage 372 of the slider 360 in step 1400. In this manner, the lens 18 of the endoscope 10 may be cleaned without removing the lens 18 and without releasing the cleaning fluid containing the debris to the surgical site. The cleaning of the lens 18 may be repeated as needed during the surgical procedure. It is also envisioned that the cleaning device 100 may be adapted for use with a robotic surgical system. For example, the robotic surgical system may activate the trigger 322, the cleaning fluid supply "FS," or the vacuum source "VS."

While the disclosure has been shown in the drawings, it is not intended that the disclosure be limited thereto, as it is intended that the disclosure be as broad in scope as the art will allow and that the specification be read likewise. Therefore, the above description should not be construed as limiting, but merely as exemplifications. Those skilled in the art will envision other modifications within the scope and spirit of the claims appended hereto.

What is claimed is:

1. A cleaning device for use with an endoscope, comprising:

a housing configured to detachably secure the endoscope thereto, the housing including an inlet port, an outlet port, and a slider configured to be slidably received in the housing;

an elongate shaft extending distally from the housing, the elongate shaft defining a lumen in communication with the housing, the elongate shaft coupled to the slider for concomitant axial displacement therewith;

an inner tube disposed within the lumen of the elongate shaft, the inner tube configured to receive the endoscope; and a suction ring coupled to a distal end portion of the elongate shaft, wherein the slider is transitionable to a first position, in which, the slider closes the inlet port and the outlet port when a lens of the endoscope is distal of the suction ring, and wherein the slider is transitionable to a second position, in which, the slider is in communication with at least the inlet port to provide a cleaning fluid when the lens of the endoscope is enclosed by the suction ring.

2. The cleaning device according to claim 1, the elongate shaft having a first groove defining an inlet channel with the inner tube and a second groove defining an outlet channel with the inner tube.

3. The cleaning device according to claim 2, wherein a distal portion of the inner tube includes a hole in fluid communication with the inlet channel, and wherein the hole is positioned to enable the cleaning fluid to enter the distal portion of the inner tube and flow across the lens of the endoscope.

4. The cleaning device according to claim 3, wherein the suction ring is configured to retain the cleaning fluid at the distal portion of the inner tube and enable the cleaning fluid to flow across the lens of the endoscope towards the outlet channel of the inner tube.

5. The cleaning device according to claim 1, wherein the outlet port of the housing is coupled to a vacuum source, and wherein the suction ring retains the cleaning fluid when the slider is in the second position.

6. The cleaning device according to claim 2, wherein the inlet channel and the outlet channel are in communication with the inlet port and the outlet port of the housing, respectively, when the slider is in the second position.

7. The cleaning device according to claim 2, wherein the slider defines a first fluid passage and a second fluid passage in communication with the inlet channel and the outlet channel, respectively.

8. The cleaning device according to claim 7, wherein the first fluid passage and the second fluid passage are in registration with the inlet port and the outlet port of the housing, respectively, when the slider is in the second position.

9. The cleaning device according to claim 1, wherein the inlet port and the outlet port of the housing are coupled to a cleaning fluid supply and a vacuum source, respectively.

10. The cleaning device according to claim 1, wherein the inner tube extends into the suction ring.

11. The cleaning device according to claim 1, wherein the suction ring includes a weakened portion configured to close an opening defined by the suction ring.

12. The cleaning device according to claim 1, wherein the slider is biased towards the first position.

13. A cleaning device for use with an endoscope, comprising:

a housing including an inlet port, an outlet port, and a slider configured to be slidably received in the housing, the slider being transitionable between a first position and a second position;

an elongate shaft extending distally from the housing, the elongate shaft coupled to the slider for concomitant axial displacement therewith, the elongate shaft defining a lumen in communication with the housing, the lumen configured to receive the endoscope; and a suction ring coupled to a distal end portion of the elongate shaft, wherein when a lens of the endoscope is distal of the suction ring, the slider is transitionable to the first position to close the inlet port and the outlet port, and wherein when the lens of the endoscope is enclosed by the suction ring, the slider is transitionable to the second position to open at least the inlet port and provide cleaning solution to the lens of the endoscope.

14. The cleaning device according to claim 13, further comprising:

an inner tube disposed within the lumen of the elongate shaft, the inner tube configured to receive the endoscope.

15. The cleaning device according to claim 14, the elongate shaft having a first groove defining an inlet channel with the inner tube and a second groove defining an outlet channel with the inner tube.

16. The cleaning device according to claim 14, wherein a distal portion of the inner tube includes a first hole in fluid communication with the inlet channel and a second hole in fluid communication with the outlet channel.

17. The cleaning device according to claim 14, wherein the suction ring is configured to retain the cleaning fluid at the distal portion of the inner tube.

18. The cleaning device according to claim 14, wherein the outlet port of the housing is coupled to a vacuum source, and wherein the suction ring retains the cleaning fluid in the inner tube when the slider is in the second position.

19. The cleaning device according to claim 13, wherein the suction ring includes a weakened portion configured to close an opening defined by the suction ring.

20. The cleaning device according to claim 13, wherein the slider is biased towards the first position.

* * * * *